United States Patent
Ohuche

(10) Patent No.: US 10,272,002 B2
(45) Date of Patent: Apr. 30, 2019

(54) ADULT DIAPER APPARATUS

(71) Applicant: Elizabeth Ohuche, New York, NY (US)

(72) Inventor: Elizabeth Ohuche, New York, NY (US)

( * ) Notice: Subject to any disclaimer, the term of this patent is extended or adjusted under 35 U.S.C. 154(b) by 263 days.

(21) Appl. No.: 15/204,893

(22) Filed: Jul. 7, 2016

(65) Prior Publication Data

US 2018/0008491 A1    Jan. 11, 2018

(51) Int. Cl.
*A61F 13/64* (2006.01)
*A61F 13/493* (2006.01)
*A61F 13/49* (2006.01)
*A61F 13/56* (2006.01)

(52) U.S. Cl.
CPC .... *A61F 13/5638* (2013.01); *A61F 13/49001* (2013.01); *A61F 13/493* (2013.01); *A61F 13/49009* (2013.01); *A61F 13/5644* (2013.01); *A61F 13/64* (2013.01)

(58) Field of Classification Search
CPC .. A61F 13/5638; A61F 13/5644; A61F 13/64; A61F 2013/5677
See application file for complete search history.

(56) References Cited

U.S. PATENT DOCUMENTS

| | | | | |
|---|---|---|---|---|
| 1,606,688 A | * | 11/1926 | Berman | A61F 13/64 604/401 |
| 2,654,367 A | * | 10/1953 | Turnham | A61F 5/4401 604/394 |
| 2,798,490 A | * | 7/1957 | Fullerton | A61F 13/64 604/397 |
| 2,800,906 A | * | 7/1957 | Hinton | A61F 5/4401 604/401 |
| 2,871,859 A | * | 2/1959 | Dunn | A61F 13/64 604/402 |
| 3,094,990 A | * | 6/1963 | Neilson | A41B 9/002 2/400 |
| 3,117,577 A | * | 1/1964 | Mosier | A61F 13/64 604/399 |
| 3,121,427 A | * | 2/1964 | Mosier | A61F 13/64 604/364 |
| 3,349,769 A | * | 10/1967 | Piekarski | A61F 13/64 604/369 |
| 3,882,870 A | * | 5/1975 | Hathaway | A41B 9/002 604/377 |
| 3,900,032 A | * | 8/1975 | Heurlen | A61F 13/505 604/394 |
| 4,352,356 A | * | 10/1982 | Tong | A61F 5/4401 604/372 |
| 4,560,380 A | * | 12/1985 | Tharel | A61F 13/53409 604/385.19 |
| 4,795,454 A | * | 1/1989 | Dragoo | A61F 13/49009 604/378 |
| 5,423,789 A | * | 6/1995 | Kuen | A61F 13/64 604/386 |

(Continued)

*Primary Examiner* — Susan S Su
(74) *Attorney, Agent, or Firm* — Law Offices of Alozie N. Etufugh, PLLC

(57) ABSTRACT

The invention features a diaper apparatus that may be adaptable for use by users of different sizes, weights etc. where the apparatus may, in one aspect of an embodiment of the present invention include the use of flaps (ties) and/or chords for, among other things, fastening and adjustment.

6 Claims, 4 Drawing Sheets

(56) References Cited

U.S. PATENT DOCUMENTS

| | | | | |
|---|---|---|---|---|
| 5,733,275 | A | * | 3/1998 | Davis ................ A61F 13/5605 604/387 |
| 6,110,157 | A | * | 8/2000 | Schmidt ............ A61F 13/5622 604/385.01 |
| 7,137,972 | B1 | * | 11/2006 | Holberg ............. A61F 13/4915 604/392 |
| D539,422 | S | * | 3/2007 | Maalouf ...................... D24/125 |
| 7,575,573 | B1 | * | 8/2009 | Roe ................. A61F 13/49011 604/385.27 |
| 7,763,003 | B1 | * | 7/2010 | Yip ..................... A61F 13/505 604/385.01 |
| 8,603,062 | B1 | * | 12/2013 | Smith ................. A61F 13/475 604/387 |
| D787,051 | S | * | 5/2017 | Gaston ....................... D24/126 |
| 2005/0038400 | A1 | * | 2/2005 | Poruthoor ........... A61F 13/493 604/385.01 |
| 2005/0038403 | A1 | * | 2/2005 | Singleton .............. A61F 13/49 604/385.13 |
| 2007/0066954 | A1 | * | 3/2007 | LaVon ............... A61F 13/4942 604/392 |
| 2009/0240228 | A1 | * | 9/2009 | Nonnenmann ... A61F 13/15593 604/385.3 |
| 2010/0280477 | A1 | * | 11/2010 | Henderson ....... A61F 13/49004 604/385.15 |

\* cited by examiner

ADULT DIAPER APPARATUS

CROSS-REFERENCE TO RELATED APPLICATIONS

This application claims the benefit of, and is related to, the following provisional patent applications: U.S. Provisional Patent Application Nos. 62/195,849 & 62/195,882 both titled "Adult Diaper Apparatus" filed Jul. 23, 2015, both of which are incorporated herein in their entireties.

FIELD OF THE INVENTION

The present invention relates, in general, to an adult diaper and in particular, an adult diaper that would fit most users.

BACKGROUND OF THE INVENTION

Different kinds of diapers exist on the market today. Some are worn by adults and have different attachments methods or configurations. However, most attachment configurations either are not meant for use by all users because they do not fit them well or they are not properly suited for use by people who do not fall into a certain size category.

As such, there is a need for a diaper that would fit most, if not all of adult diaper users. There is also a need for a diaper that would be able to maintain its size, function and position once worn.

SUMMARY OF THE INVENTION

An aspect of an embodiment of the present invention contemplates an adult diaper apparatus which may include: an absorbent material section, flap(s) extending from a first edge of the absorbent material section, where each flap(s) is structurally configured to be tied with another flap which extends from a second edge of the absorbent material section, and where the first edge is opposite the second edge and an elastic band each along, surrounding the outer edges of the absorbent material section. In this disclosure, the term "flap" may be used interchangeably with the term "tie".

Another aspect of an embodiment of the present invention contemplates an adult diaper apparatus which may include a front section and a rear section, where each section may include a number of corners, an absorbent material section located between and connecting both front and rear sections, tie(s) at the end of each corner, and an elastic band each along, surrounding and/or within the outer edges of both front and rear sections.

In an aspect of an embodiment of the present invention, the absorbent material section may include absorbent material affixed onto an impermeable substrate.

In an aspect of an embodiment of the present invention, the absorbent material section may be rectangular in shape. In an aspect of an embodiment of the present invention, each corner of the absorbent section may extend into a triangular section.

In an aspect of an embodiment of the present invention, two ties extend from each corner of the rectangular absorbent section.

In an aspect of an embodiment of the present invention, one of the front section corner ties may be configured/structurally designed to extend to a rear section corner tie which is linearly aligned with the front section corner tie.

In an aspect of an embodiment of the present invention, the diaper apparatus may be held in place by the tying arrangement between the corner ties and the rear ties which are linearly aligned in relation to the corner ties and the tying arrangement between the remaining front and rear ties.

In an aspect of an embodiment of the present invention, each of the front and rear sections may include one or more sets of ties.

In an aspect of an embodiment of the present invention, the diaper apparatus may be held in place by the tying arrangement between a first tie of the first set of ties of the front section and a first tie of the first set of ties of the rear section, a tie between the second tie of the first set of ties of the front section, a tie between the second tie of the first set of ties of the front section and the first tie of the second set of ties of the front section, a tie between a second tie of the second set of ties of the front section and a second ties of the second set of ties of the rear section, a tie between a first tie of the second set of ties of the rear section and a second tie of the first set of ties of the rear section.

In an aspect of an embodiment of the present invention, both first set of ties of the front section and the first set of ties of the rear section may be linearly aligned with each other.

In an aspect of an embodiment of the present invention, both second set of ties of the front section and the second set of ties of the rear section may be linearly aligned with each other.

In an aspect of an embodiment of the present invention, none of the fastening ties are between any sets of ties that are diagonally across from each other.

Another aspect of an embodiment of the present invention contemplates an adult diaper apparatus which may include a front section and a rear section, where each section may include a number of corners, an absorbent material section located between, and connecting both front and rear sections, at least one tie at the end of each corner, an elastic band each along/surrounding/within the outer edges of both front and rear sections, and channel(s) extending across each of the front section and the rear section.

In another aspect of an embodiment of the present invention, the diaper apparatus may include a chord running within each of the channel(s) of the front and rear sections, where each chord has a first and a second end and each end extends out of each channel by way of a slit/opening.

In another aspect of an embodiment of the present invention, the apparatus may be fastened, held in place and/or tightened by a combination of ties between, at the very least, the first chord end of the front section chord and the first chord end of the rear section chord, a tie between the second chord end of the front section and the second chord end of the rear section chord.

A further aspect of an embodiment of the present invention contemplates an adult diaper apparatus which may include a front section and a rear section, where each section may include a number of corners, an absorbent material section located between and connecting both front and rear sections, at least one tie at the end of each corner, an elastic band each along/surrounding/within the outer edges of both front and rear sections, and channel(s) extending across each of the front section and the rear section.

In a further aspect of an embodiment of the present invention, the diaper apparatus may include at least two chords running within each of the channel(s) of the front and rear sections, where each chord has a first and a second end for the first chord within the channel and a first and a second end for a second chord within the channel and each end extends out of each channel by way of a slit/opening.

In a further aspect of an embodiment of the present invention, the apparatus may be held in place and tightened by a combination of ties between, at the very least, a first chord end of a second chord of the front section and a first chord end of a first chord of the rear section, a tie between the second chord end of the second chord of the front section and the second chord end of the first chord of the rear section, a tie between the first and second chord ends of the first chord of the front section and a tie between the first and second chord ends of the second chord of the rear section.

In a further aspect of an embodiment of the present invention, the first chord end of a second chord of the front section and the first chord end of a first chord of the rear section are linearly aligned with each other.

In a further aspect of an embodiment of the present invention, the second chord end of the second chord of the front section and the second chord end of the first chord of the rear section are linearly aligned with each other.

In a further aspect of an embodiment of the present invention, none of the ties may be between any sets of chord ends that are diagonally across from each other.

A yet further aspect of an embodiment of the present invention contemplates an adult diaper apparatus which may include a first layer of material, an absorbent material section superimposedly mounted onto a section of the first layer of material and elastic bands each along/surrounding outer edge sections of the absorbent material section.

In a yet further aspect of an embodiment of the present invention, the absorbent material section may be rectangular in shape.

In yet a further aspect of an embodiment of the present invention, the first layer of material upon which the absorbent material section is superimposedly mounted may also be rectangular in shape. In this aspect, the first layer of material may be bordered by four tie ends at its ends/corners which may be used to secure the apparatus onto a user.

DETAILED DESCRIPTION OF THE INVENTION

Figure 1A:
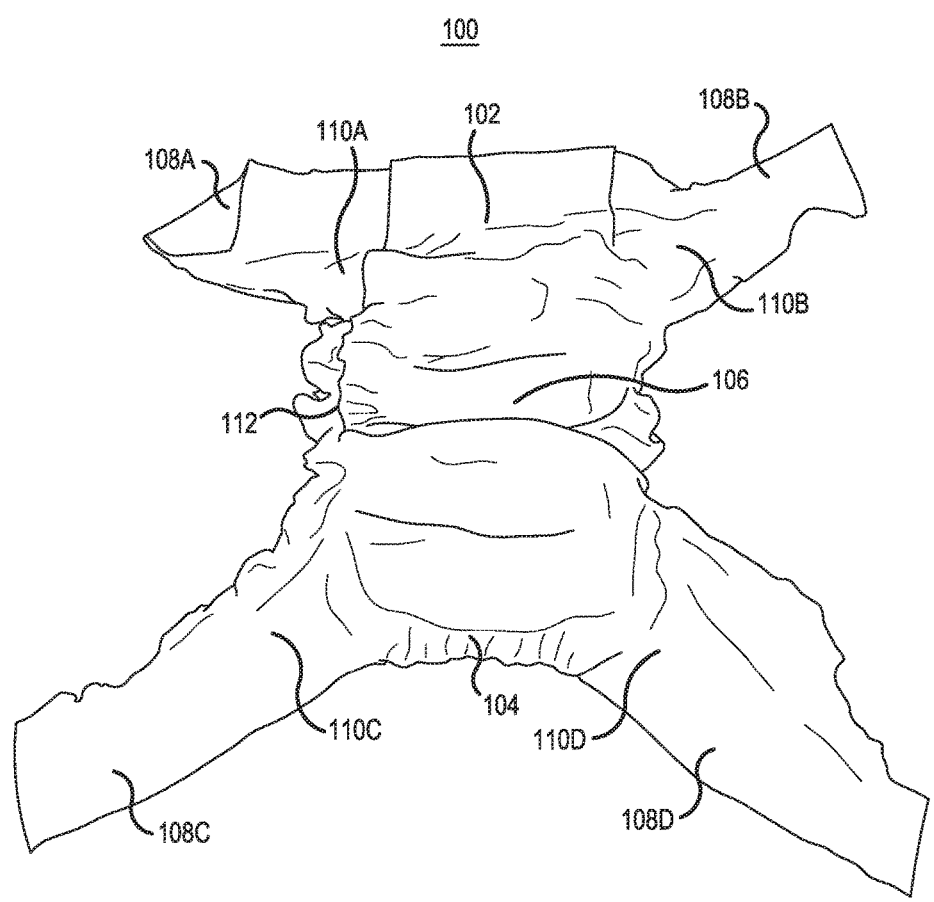
FIG. 1A illustrates an exemplary diaper apparatus according to an aspect of an embodiment of the present invention.
Figure 1B:
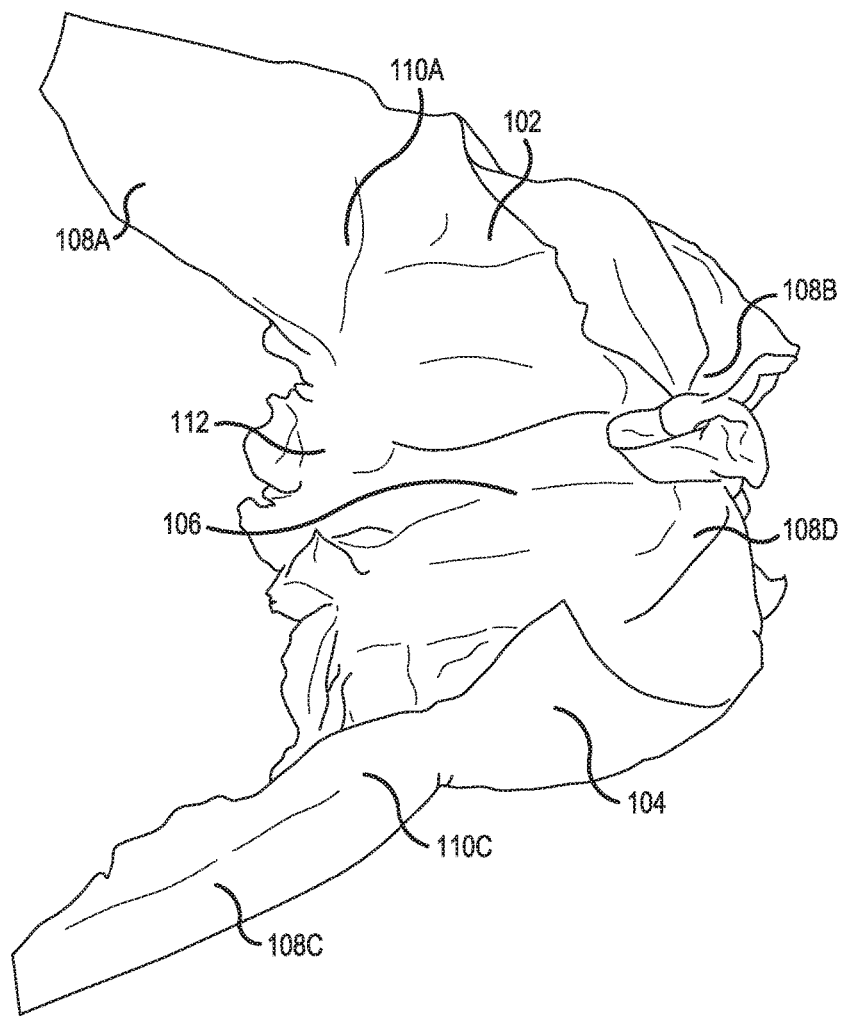
FIG. 1B illustrates the diaper apparatus with an illustration of a tie between flaps according to an aspect of an embodiment of the present invention.

Referring now to FIGS. 1A and 1B, an exemplary diaper apparatus 100 is shown according to an aspect of an embodiment of the present invention. Diaper apparatus 100 may include a front section 102 and rear section 104, where each section may include a number of corners 110A through 110D. Diaper apparatus 100 may also include absorbent material section 106 located between and, in one aspect of an embodiment of the present invention, connecting both front (102) and rear (104) sections. In an aspect of an embodiment of the present invention, absorbent material section 106 may include absorbent material affixed onto an impermeable substrate which prevents leakage.

Diaper apparatus 100 may also include tie(s) 108A through 108D each at the end of each corners 110A through 110D, and elastic band 112 each along/surrounding or, in another aspect, within the outer edges of both front 102 and rear 104 sections. In another aspect of an embodiment of the present invention, elastic band 112 may extend along the periphery of one or more sides of absorbent material section 106.

In an aspect of an embodiment of the present invention, absorbent material section 106 may be rectangular in shape. In an aspect of an embodiment of the present invention, each corner 110A through 110D of rectangular absorbent section 106 may extend into a triangular section.

Figure 2:
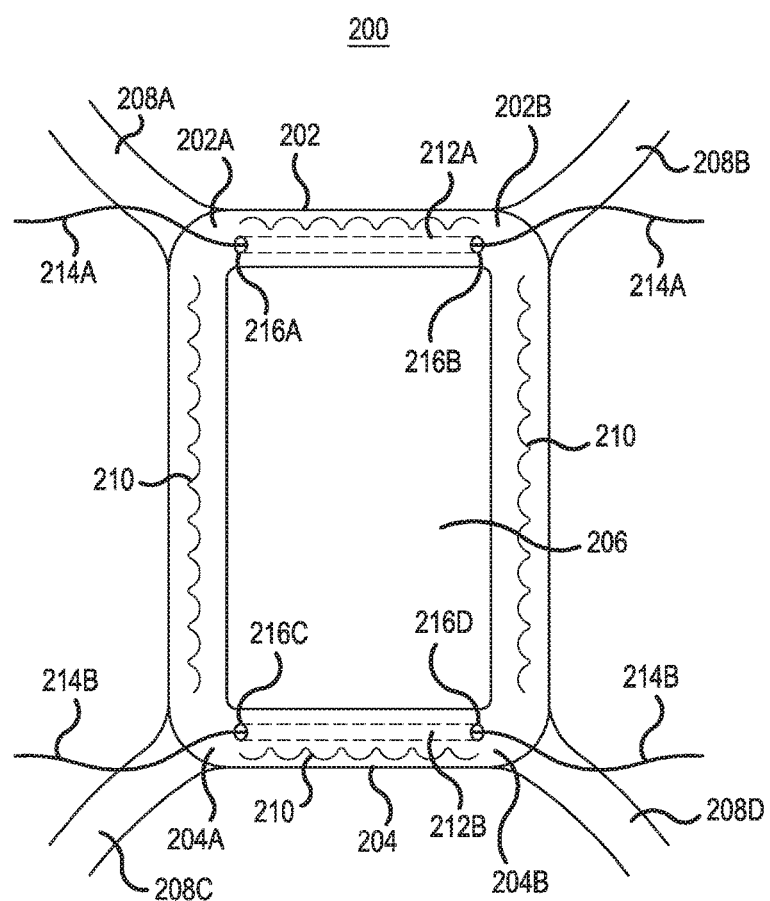
FIG. 2 illustrates another exemplary diaper apparatus showing its elements according to an aspect of an embodiment of the present invention.

In an aspect of an embodiment of the present invention, two ties 108A and 108B of front section 102, may respectively extend from corners 110A and 110B of absorbent section 106. Ties 108A and 108B may be configured/structurally designed to respectively extend to ties 108C and 108D, respectively, of rear section 104 as illustrated in FIG. 2. Accordingly, diaper apparatus 100 when worn by a user, may be held in place by the tying arrangement between corner ties 108A & 108C and ties 108B & 108D where ties 108A and 108C are linearly aligned in relation to each other and ties 108B and 108D are also linearly aligned with each other.

In another aspect of an embodiment of the present invention, each of front (102) and rear (104) sections of diaper apparatus 100 may include multiple sets of ties—for instance two or more sets of ties in front section 2102 and the same for rear section 104.

Referring now to FIG. 2, a diaper apparatus 200 is shown according to an aspect of an embodiment of the present invention. Here, diaper apparatus 200 may include front section 202 and rear section 204, where each section may include corners 202A, 202B, 204A and 204B, where corners 202A and 202B represent the corners for front section 202 and corners 204A and 204B represent the corners for rear section 204. Diaper apparatus 200 may include absorbent material section 206 located between and connecting both front (202) and rear (204) sections of diaper apparatus 200. In an aspect of an embodiment of the present invention and extending from each corner is or more ties which may be used to fasten diaper apparatus 200 when in use. In one aspect, tie 208A may extend from corner 202A, tie 208B may extend from corner 202B, tie 208C may extend from corner 204A and tie 208D may extend from corner 204B. In one aspect of an embodiment of the present invention, diaper apparatus 200 may include elastic band 210 which may extend along or surrounding the outer edges of both front (202) and rear (204) sections. In another aspect of an embodiment of the present invention, elastic band 210 may extend along the periphery of one or more sides of absorbent material section 206. Diaper apparatus 200 may additionally include channels 212A and 212B respectively extending across each of front section 202 and rear section 204. Channels 212A and 212B may each respectively include chords 214A and 214B running within each of the channels of the front and rear sections, where each chord has a first and a second end and each end extends out of each channel by way of a slit/opening. For instance, front section 202 may have channel 212A which in turn may include chord 214A which extends through channel 212A out through slits/openings 216A and 216B.

In another aspect of an embodiment of the present invention, diaper apparatus 200 may be held in place and tightened by a combination of ties between, at the very least, chords which are linearly aligned with each other—for instance, a tie between the end of chord 214A which extends from opening 216A and its ties with chord 214B which extends from opening 216C. The same goes for a tie between the end of chord 214A which extends from opening 216B and its tie with the end of chord 214B which extends from opening 216D.

Figure 3:
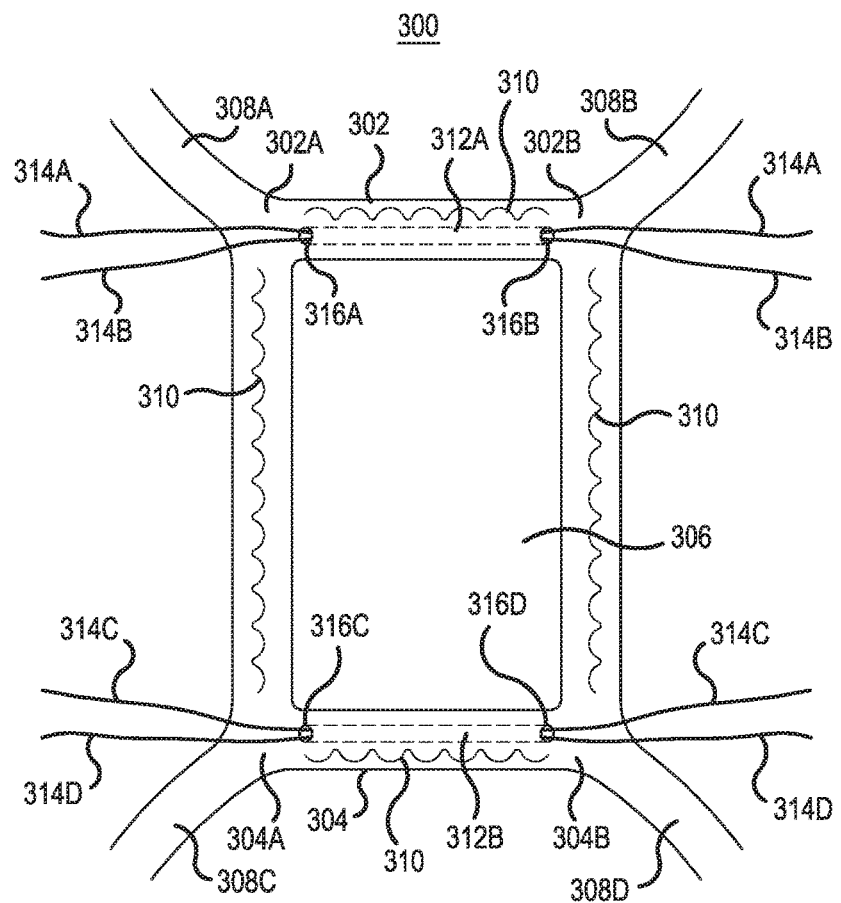
FIG. 3 illustrates a further exemplary diaper apparatus showing its elements according to an aspect of an embodiment of the present invention.

Referring now to FIG. 3, another diaper apparatus 300 is shown according to an aspect of an embodiment of the present invention. Here, diaper apparatus 300 may include front section 302 and rear section 304, where each section may include corners 302A, 302B, 304A and 304B, where corners 302A and 302B represent the corners for front section 302 and corners 304A and 304B represent the corners for rear section 304. Diaper apparatus 300 may include absorbent material section 306 located between and connecting both front (302) and rear (304) sections of diaper apparatus 300. In an aspect of an embodiment of the present invention and extending from each corner is one or more ties which may be used to fasten diaper apparatus 300 when in use. In one aspect, tie 308A may extend from corner 302A, tie 308B may extend from corner 302B, tie 308C may extend from corner 304A and tie 308D may extend from corner 304B. In one aspect of an embodiment of the present invention, diaper apparatus 300 may include elastic band 310 which may extend along or surrounding the outer edges of both front (302) and rear (304) sections. In another aspect of an embodiment of the present invention, elastic band 310 may extend along the periphery of one or more sides of absorbent material section 306. Diaper apparatus 300 may additionally include channels 312A and 312B respectively extending across each of front section 302 and rear section 304. Channel 312A may include chords 314A and 314B running through it while channel 312B may include chords 314C and 314D running through it. Channels 312A and 312B may each have a set of openings 316A through 316D through which chords 314A and 314B (for front section 302) and chords 314C and 314D (for rear section 304) exit. For front section 302, channel 312A may have openings 316A and 316B while channel 312B of rear section 304 may have openings 316C and 316D.

Chords 314A through 314D may be used to fasten diaper apparatus 300 in place when in use. For instance, one end of chord 314A (exiting opening 316A) may be tied with the second end of chord 314A (exiting opening 316B) to fasten the front section of apparatus 300, while one end of chord 314B (exiting opening 316A) may be tied with one end of end of chord 314C (exiting opening 316C). In an aspect of an embodiment of the present invention, similar ties complete the fastening of diaper apparatus 300 i.e. having the second end of chord 314C (exiting opening 316D) tied with the second end of chord 314B (exiting opening 316B) and having the first end of chord 314D (exiting opening 316C) tied with its second end (exiting opening 316D) to secure the rear section 304 of apparatus 300.

In one aspect of an embodiment of the present invention, diaper apparatus 300 may have ties 308A through 308D in addition to chords 314A through 314D. In another aspect of an embodiment of the present invention, diaper apparatus 300 may have either set of ties 308A through 308D or chords 314a through 314D for the fastening of diaper apparatus 300.

In a further aspect of an embodiment of the present invention, none of the ties may be between any sets of chord ends that are diagonally across from each other.

The invention has been described in detail with particular reference to certain preferred embodiments thereof, but it will be understood that variations and modifications can be effected within the spirit and scope of the invention.

What is claimed is:

1. An adult diaper apparatus comprising:
   a front section and a rear section, wherein each section comprises of a number of corners;
   an absorbent material section located between and connecting both front and rear sections;
   at least one tie at the end of each corner;
   an elastic band each along the outer edges of both front and rear sections;
   channels extending across each of the front section and the rear section; and
   a chord running within each of the channels of the front and rear sections, wherein each chord has a first and a second end and each end extends out of each channel by way of a slit/opening.

2. The diaper apparatus of claim 1 wherein the apparatus is held in place and tightened by a combination of ties between, at the very least, a first chord end of the front section and a first chord end of the rear section, a tie between the second chord end of the front section and the second chord end of the rear section.

3. The diaper of claim 1 further comprising at least two chords running within each of the channels of the front and rear sections, wherein each chord has a first and a second end for the first chord within the channel and a first and a second end for a second chord within the channel and each end extends out of each channel by way of a slit/opening.

4. The diaper apparatus of claim 3 wherein the apparatus is held in place and tightened by a combination of ties between, at the very least, a first chord end of a second chord of the front section and a first chord end of a first chord of the rear section, a tie between the second chord end of the second chord of the front section and the second chord end of the first chord of the rear section, a tie between the first and second chord ends of the first chord of the front section and a tie between the first and second chord ends of the second chord of the rear section.

5. The diaper apparatus of claim 4 wherein the first chord end of a second chord of the front section and the first chord end of a first chord of the rear section are linearly aligned with each other.

6. The diaper apparatus of claim 4 wherein the second chord end of the second chord of the front section and the second chord end of the first chord of the rear section are linearly aligned with each other.

* * * * *